United States Patent [19]

Zajic et al.

[11] 4,355,109
[45] Oct. 19, 1982

[54] MICROBIOLOGICAL PRODUCTION OF NOVEL BIOSURFACTANTS

[76] Inventors: James E. Zajic, The University of Texas, El Paso, Tex. 79968; Donald F. Gerson, Basel Institute for Immunology, 487 Grenzacherstrasser, Ch-4005, Basel 5, Switzerland; Richard K. Gerson, Micro-Biology Department, MacDonald College, McGill University, St. Anne du-Bellevue, Montreal, Quebec, Canada, H3C 3G1; Chandrakant J. Panchal, Brewery Research, Labatt Breweries, 150 Simcoe St., London, Ontario, Canada, N6A 4M3

[21] Appl. No.: 142,779

[22] Filed: Apr. 22, 1980

[30] Foreign Application Priority Data

Apr. 23, 1979 [CA] Canada ................................. 326112

[51] Int. Cl.$^3$ ............................................. C12P 1/04
[52] U.S. Cl. .................................. 435/170; 435/249; 435/253; 435/843

[58] Field of Search ................. 435/68, 101, 134, 170, 435/248–250, 253, 830, 843, 872; 536/1; 260/112, 236.5

[56] References Cited

U.S. PATENT DOCUMENTS 3,709,783  1/1973  Tanaka et al. ...................... 435/830
3,997,398 12/1976  Zajic et al. ........................... 435/101

OTHER PUBLICATIONS

Condensed Chemical Dictionary, 8th Ed., Hawley, pp. 840, 841, Van Nostrand, N.Y.

Primary Examiner—Hiram Bernstein
Attorney, Agent, or Firm—Fleit & Jacobson

[57] ABSTRACT

Newly isolated microbes of the genera Arthrobacter-Corynebacterium-Nocardia as represented by Corynebacteria Salvinicum strain SFC, produce substantial quantities of materials having outstanding surfactant properties, when grown on carbon supplying substrates under fermentation conditions.

6 Claims, No Drawings

MICROBIOLOGICAL PRODUCTION OF NOVEL BIOSURFACTANTS

This invention relates to microbiological production of surfactant materials, to novel surface active materials (surfactants) of microbiological origin, and to microorganisms capable of production of surfactant materials.

Surface active agents are used in soaps and industrial cleaners, in tertiary oil recovery, in flotation, in emulsions, in foods, etc. Synthetic surfactants tend to dominate the market, however in recent years microbes have been found to produce surfactants. Many of these biological surfactants have the advantage of being biodegradable, possessing low toxicity and high specificity for certain types of uses.

U.S. Pat. No. 3,997,398, J. E. Zajic and E. Knettig, describes in detail the production, testing and utility of surfactant materials of microbiological origin.

The present invention is based on the discovery of a certain class of microbes which can be grown by aerobic fermentation processes under controlled conditions to give materials of outstanding surfactant properties, in high yields. The microbes are certain cultures from the *Arthrobacter-Corynebacterium-Nocardia* Genera which are characterized by their ability to metabolize the protective waxy hydrocarbon material found naturally on the plant cuticles of water plants such as salvinia, to expose the plant to disease-causing infections. The cultures are represented by a culture first isolated by us and referred to herein as *Corynebacterium salvinicum* strain SFC.

Thus, according to one aspect of the present invention, there is provided a process for microbiological production of surfactant materials, which comprises cultivating by aerobic fermentation, in a growth promoting medium and under growth promoting conditions, and on a carbon-containing substrate, a microbial strain of a culture from the genera Arthrobacter, Corynebacterium and Nocardia, said microbial strain being characterized by ability to metabolize the waxy protective coating of the plant cuticles of Salvinia water plant under normal growth conditions for the microbial strain; to produce a surfactant material of microbiological origin in said fermentation medium.

A specific preferred microbial strain, representative of those useful in the present invention, is *Corynebacterium Salvinicum* strain SFC. This is believed novel and not previously disclosed. A viable sample of this culture has been deposited in the International Collection of Phytopathogenic Bacteria, University of California, Davis, and has been given the reference number ICPB 4312 (Cooper SFC).

It is preferred to use hydrocarbons as the carbon-containing substrate in the process of the invention, especially liquid aliphatic paraffinic hydrocarbons, straight chain or branched chain. Most preferably, the hydrocarbons have from about 6 to about 18 carbon atoms per molecule. Mixtures of hydrocarbons such as kerosene can be used also. In addition, the microbes will grow on other carbon substrates such as carbohydrates and sodium acetate, but normally with less desirable results in the process of the invention.

On a small scale, the *Corynebacterium salvinicum* culture used here can be grown by aqueous culture in shake flasks (500 ml), carboys (16 liter), or fermentors (28, 48 liters) for the production of surfactant. The aqueous cultivation medium is important. It should contain the proper balance of minerals, especially inorganic nitrogen, phosphate and potassium as well as other minerals and trace minerals required for growth of cells. The energy source for growth is preferably kerosene or aliphatic hydrocarbons representing the homologous series: undecane, dodecane, tridecane, tetradecane, pentadecane, hexadecane, heptadecane and waxy hydrocarbons. The pH range for this process varies from 4 to 8.8 depending on the inorganic nitrogen source and buffer system used. The system is an aerobic process, thus either air or oxygen must be supplied in adequate amounts required for growth and product formation. Mixing is accomplished by shaking in small laboratory vessels, however in larger vessels the mixing required should be in the low to high turbulent range. (Reynolds number of 1000 to 10,000). The optimal temperature is around 30° C., but high yields can be obtained over the temperature range of 18° to 37° C.

In the process for producing the surfactants according to the present invention, it is preferred to use a concentration of hydrocarbon in the range from 0.5 to 9.0% (W/V). Inorganic salts beneficial to the surfactant production of the system of the present invention includes sodium nitrate, ammonium sulphate, ammonium chloride, ammonium nitrate, ammonium carbonate and urea. As disclosed herein below, inorganic nitrogen compounds are beneficial to the surfactant production in the present process, the preferred range of concentrations of inorganic nitrogen being from 0.1 to 4.0% (W/V), with the most preferred range being from about 0.6 to 4.0% (W/V). It is also desirable to include vitamins and essential nutrients in the fermentation medium of the present invention, by adding yeast extract and nutrient broth. Most beneficial ranges of concentrations for these materials are 0.1–3% (W/V), with optimum results at 0.1–2.0% concentration (W/V).

According to a further aspect of the process of the present invention, it has been found that isonicotinic acid hydrazide inhibits production of surfactant. This material is available under the trade name "Isoniazid". It is used in treatment of tuberculosis, a disease caused by the microbe *Mycobacterium tuberculosis.* It specifically inhibits mycolic acid production. However, it has been found that, if a small amount of surfactant of the synthetic type, such as Tween 80 is added, the combination of both reagents, isonicotinic acid hydrazide and Tween 80, increases the production of surfactant by the *Corynebacterium Salvinicum* microbe several fold.

According to another aspect of the process of the present invention, the enzyme lysozyme can be used, for treatment of the cells produced in the fermentation process, either after fermentation is completed or during the fermentation, to obtain a further significant increase in surfactant concentration. Preferred concentrations of lysozyme for this purpose are in the range 0.005–0.01%, (W/V).

According to a further aspect of the present invention, diethoxymethane can be added to the fermentation broth, to obtain a beneficial effect on surfactant production. Moreover, the total biomass produced in the presence of diethoxymethane is increased. Its effect on cell morphology is quite pronounced.

Culture Characteristics of *Corynebacterium Salvinicum* Strain SFC

The bacterial strain *Corynebacterium salvinicum* SFC was isolated from a plant source and was considered to be a plant pathogen. It is a Gram positive rod-form pleiomorphic organism that grows mainly in the oil phase. When in mid log phase its dimensions are about 2.5 µm ×1 µm. It is non-motile and does not form chains. On 1.25% nutrient agar plates the colonies are dry.

*Corynebacterium salvinicum* grows well on most aliphatic hydrocarbons from $C_{10}$-$C_{18}$. Hexadecane was required as a substate for good surfactant production. Taxonomic characteristics of this culture are summarized below, and the growth characteristics on several substrates are shown in Example 2.

Morphological and Biochemical Characteristics of *Corynebacterium salvinicum* Strain SFC

General Characteristics

Source: isolated from plant source as a pathogen
Gram stain: Gram positive
Size: about $2.5\mu \times 1\mu$
Motility: non-motile
Colony on agar: on nutrient agar colonies are dry and star-shaped, on yeast glucose agar the colonies are dull, rough and creamy coloured.
Growth characteristics: optimum temperature 28°–30° C., no growth occurs at 37° C. on plates. There is no anaerobic growth. No soluble pigment was produced.
Microscopic: 18 hr.-growth produces Gram positive diptheroid appearing rods, 72 hr.-growth has predominantly coccoid forms also with long forms which appear to branch or divide by "snapping division".

Biochemical Characteristics

Nitrate reduction: positive
Citrate utilisation: positive
Glucose fermentation: negative (positive growth only)
Catalase: positive (very strongly) Starch hydrolysis: positive

| Antibiotic Sensitivity Tests (Disk Test) | | |
|---|---|---|
| Antibiotic | Concentration | Inhibition after Four Days |
| Penicillin | 10 units | None |
| Penicillin G | 10 units | 7mm |
| Tetracycline | 30 mcg | 6–8mm |
| Sulfisoxole | 300 mcg | 2.5cm |
| Methicillin | 5 mcg | None |
| Kanamycin | 30 mcg | 7mm |
| Ampicillin | 10 mcg | 8mm |
| Cephaloridine | 30 mcg | 2.2–2.5cm |
| Clindamycin | 2 mcg | None |
| Chloramphenical | 30 mcg | 4–6mm |
| Carbenicillin | 100 mcg | 8mm |
| Erythromycin | 15 mcg | 1cm |
| Gentamicin | 10 mcg | 2–4mm |
| Neomycin | 30 mcg | 2.5–3mm |
| Streptomycin | 10 mcg | 3–4mm |
| Polymyxin B | 300 units | None |
| Erythromycin | 15 mcg | 8mm |
| Isoniazid | 50 mg/ml | Inhibited |

The fermentation medium of choice contains all essential minerals required for growth as well as hydrocarbon which is a source of energy. A portion of the hydrocarbon is also used in surfactant production. It also induces surfactant production. One such media is described below:

| Mineral Salts Medium | g/liter |
|---|---|
| $NH_4SO_4$ | 2 |
| $KH_2PO_4$ | 4 |
| $Na_2HPO_4$ | 6 |
| $MgSO_4.7H_2O$ | 0.2 |
| $CaCl_2.2H_2O$ | 0.001 |
| $FeSO_4.7H_2O$ | 0.001 |

Adjust to desired pH 6.5–8.0
Hydrocarbon, Kerosene or aliphatic hydrocarbon 5 to 160 g The amounts of minerals required should be such that all requirements for growth and product formation are satisfied.

Biosurfactant Evaluation

Surfactants are known to decrease the surface tension when added to water. As the concentration of surfactant increases, the surface tension (ST) in dynes/cm (or mN/m) decreases to some minimal level until no further decrease is seen. Commonly this point ranges for most surfactants between 28–60 dynes/cm. The point or concentration at which additional increments of surfactant do not give additional decreases in ST is known as the critical micelle concentration (CMC), and it is quite specific for a given surfactant. If more than one surfactant is formed, several CMC values may be observed, particularly if each surfactant has a different CMC.

The identification of the CMC values is important. In the process of the invention, the actual yield of the surfactant or combination of surfactants can be obtained by a serial dilution technique, in which the production broth is diluted with water until the CMC value is reached. The greater the dilution required, the greater the concentration of surfactant produced and present in the broth. The apparent CMC of the whole fermentation broth is a measure of the concentration of surfactant present in the broth. To effect measurements and obtain CMC values for the whole broth, the whole fermentation broth may be diluted consecutively by a factor of 2 or 1.5, and surface tension measured and plotted as a function of the $\log_{10}$ of the broth concentration. With a novel substance or one of which the composition is not known with precision, the concentration of surfactant in absolute units cannot be determined. It is however possible to obtain figures of concentration of surfactant in units of the critical micelle concentration, which is related to the absolute concentration through an arbitrary constant. The reciprocal of the dilution required to reach the CMC indicates the concentration of surfactant in the whole broth in units of the CMC of that surfactant. Thus the reciprocal of dilution value at CMC is used as a measure of the concentration of surfactant times the CMC value of the surfactant or surfactants.

Surface tensions of the whole fermentation broths were determined using a Fisher Autotensiomat, which is a modified deNuoy surface tensionmeter with a motorized sample stage and a strain gauge which measures tension on the platinum ring. Output is directly in dynes/cm. The platinum ring is pulled upwardly through the aqueous solution, recording a plot of displacement against tension. The maximum tension value on the curve, which is obtained as the ring passes through the liquid surface, is the surface tension value.

The results are given in Table II.

The process and product of the present invention are further illustrated in the following specific examples.

EXAMPLE 1

The more important cultures developed and used for biosurfactant production in this study were taken and grown in a mineral salts medium with either kerosene or hexadecane and the concentration of surfactant produced, in terms of the most concentrated surfactant, evaluated. The data, along with the Gibbs surface excess, is shown below.

|  | Surfactant Concentration* × CMC | Gibbs Surface Excess p moles/cm$^2$ |
|---|---|---|
| Corynebacterium salvinicum (SFC) | 30,000 | 466 |
| Corynebacterium lepus | 3,030 | 2,100 |
| Corynebacterium fasciens | 75 | 1,050 |
| Corynebacterium hydrocarboclastus | 8 | 1,300 |
| Corynebacterium xerosis | 7 | 800 |
| Nocardia erythropolis | 150 | 1,000 |

*maximum value observed

EXAMPLE 2

Normally kerosene is the preferred source of hydrocarbon for surfactant production, however all of the aliphatic hydrocarbons can be used in the production of surfactant. The following hydrocarbons were tested at a concentration of 3% (volume hydrocarbon to volume of aqueous medium), however they can be added over a wide range of concentrations and give slightly better or poorer results. The pH used was 7.0.

|  | Biomass g/l | Surfactant Concentration | | Surface or Interfacial Tension* | |
|---|---|---|---|---|---|
|  |  | × CMC$_1$ | × CMC$_2$ | ST | IT |
| decane | .922 | 161 | 83 | 30 | 1.0 |
| undecane | .874 | 27 | 16 | 34 | 1.0 |
| dodecane | .804 | 74 | 16 | 31 | 2.0 |
| tridecane | 1.152 | 76 | 37 | 30 | 1.0 |
| tetradecane | 1.312 | 80 | 44 | 29 | 1.5 |
| pentadecane | 1.272 | 43 | 15 | 31 | 3.0 |
| hexadecane | ND | 434 | 98 | ND | ND |

*Interfacial tension measured against hexadecane
ND: Not determined

Other carbon sources also support growth of *Corynebacterium salvinicum* SFC. The growth and surfactant production obtained with 5 of these is given below. Sodium acetate is a poor carbon source for surfactant production, while hexadecane is an excellent source. Combination of these 2 substrates shows that sodium acetate is not an inhibitor of growth or surfactant production; indeed, additional biomass can be obtained with the addition of sodium acetate to a hexadecane-based culture medium.

Growth of *Corynebacterium salvinicum* Strain SFC on various carbon sources at 25°±2° C. in 500 ml Erlenmeyer shake flasks. Duration of growth was 3 days.

| Carbon Source | Total Biomass (gm/l) | Surfactant Concentration × CMC |
|---|---|---|
| Fructose, 3% w/v | 1.62 | 1.5 |
| Glucose, 3% w/v | 2.00 | 2.2 |
| Sodium acetate, 3% w/v | 0.65 | 2 |
| Sodium acetate, 1.5% w/v plus hexadecane, 1.5% v/v | 4.38 | 82 |
| Hexadecane, 3% v/v | 2.80 | 95 |

EXAMPLE 3

Since hexadecane gave such high yields of surfactant, it was investigated over a much broader range of concentrations. The standard mineral salts broth was used and the concentrations (%) of hexadecane tested were: 0.5, 1.0, 2.0, 3.0, 4.0, 5.0, 7.0 and 9.0% (v/v). The initial pH of the broth was 7.0. The concentration of surfactant in terms of the CMC values is reported below.

| Hexadecane v/100 ml broth | Surfactant Concentration | |
|---|---|---|
|  | × CMC$_1$ | × CMC$_2$ |
| 0.5 | — | 19 |
| 1.0 | 434 | 98 |
| 2.0 | 1,190 | 270 |
| 3.0 | 6,670 | 800 |
| 4.0 | 3,450 | 833 |
| 5.0 | * | 833 |
| 7.0 | 3,450 | 880 |
| 9.0 | 5,000 | 869 |

*Sample spilled

The optimal concentration of hexadecane was 3.0% (v/v), however high levels of surfactants were produced over the range of 1.0 to 9.0% (w/v) of hexadecane.

EXAMPLE 4

The selection of the source of nitrogen used for growth and product formation is an exacting requirement in a fermentation process. The inorganic salts tested were ammonium sulfate, sodium nitrate, ammonium chloride, ammonium nitrate, ammonium carbonate and urea. The range of concentrations tested were from 0.06 to 6.0% (w/v).

| Nitrogen Compound Tested (Initial pH 6.9) | Surfactant | Source of Nitrogen (percent) Concentration (g/v) | | | | | | | | | |
|---|---|---|---|---|---|---|---|---|---|---|---|
|  |  | .06 | .1 | .3 | .6 | 1.0 | 2.0 | 3.0 | 4.0 | 5.0 | 6.0 |
|  |  | Concentration of Surfactant in Terms of CMC × CMC | | | | | | | | | |
| NaNO$_3$ | CMC$_1$ | 1.7 | 10 | 30 | 69 | 3.9 | 144 | 90 | ND | 58 | |
|  | CMC$_2$ | 18 | 40 | 172 | 167 | 74 | 278 | 384 | ND | 175 | |
| (NH$_4$)$_2$SO$_4$ | CMC$_1$ | — | 122 | 952 | 666 | 1250 | ND | 526 | ND | 769 | |
|  | CMC$_2$ | — | 33 | 71 | 113 | 454 | ND | 70 | ND | 118 | |
| NH$_4$Cl | CMC$_1$ | — | 80 | 115 | 526 | 1520 | 1640 | 1920 | ND | 1850 | |
|  | CMC$_2$ | — | 26 | 31 | 125 | 769 | 606 | 465 | ND | 333 | |
| NH$_4$NO$_3$ | CMC$_1$ | 91 | 173 | 49 | 119 | — | 2780 | 4000 | ND | ND | |
|  | CMC$_2$ | 37 | 34 | 17 | 28 | — | 1000 | 1110 | ND | ND | |
| NH$_4$CO$_3$ | CMC$_1$ | 38 | 44 | 87 | 85 | 769 | 285 | 200 | ND | ND | |
|  | CMC$_2$ | 3.6 | 4.7 | 12 | 18 | 114 | 105 | 43 | ND | ND | |
| Urea | CMC$_1$ | 41 | 51 | 74 | 370 | 909 | 1490 | 250 | ND | ND | ND |
|  | CMC$_2$ | 8 | 8.7 | 9.9 | 103 | 169 | 307 | 39 | ND | ND | ND |

All of the inorganic nitrogen sources reported herein supported some growth and production of both surfactants $CMC_1$ and $CMC_2$. The ammonium chloride and ammonium nitrate systems were the most beneficial to surfactant production at the initial pH used which was 6.9 in most instances. Urea and ammonium sulfate were next best and sodium nitrate and ammonium carbonate gave the poorest results. Since salts of sodium nitrate tend to increase the pH during utilization of nitrate and salts of ammonium tend to decrease pH during their utilization, pH was chosen as a variable for further study. Nitrate appears to influence and increase $CMC_2$ much more than it does $CMC_1$.

EXAMPLE 5

Vitamin and essential nutrient supplement.

Yeast extract and nutrient broth contain a number of complex vitamins, some minerals and even some amino acids which are required for growth. Both of these were added over a specified range (0.3–6.0% wt/v) to the mineral salts-kerosene medium. The initial pH was 7.0.

| Complex Nutrient Supplement | Surfactant Synthesized | Concentration Tested (%, wt/v) | | | | | | | | | |
|---|---|---|---|---|---|---|---|---|---|---|---|
| | | .06 | .1 | .3 | .6 | 1.0 | 2.0 | 3.0 | 4.0 | 5.0 | 6.0 |
| Yeast Extract | $CMC_1$ | 454 | 1190 | 1920 | 487 | 1960 | 323 | 606 | ND | ND | ND |
| | $CMC_2$ | 139 | 274 | 159 | 117 | 147 | 164 | 294 | ND | ND | ND |
| Nutrient Broth | $CMC_1$ | ND | ND | 1587 | 1492 | 1754 | 2440 | 200 | 380 | 217 | 208 |
| | $CMC_2$ | ND | ND | 645 | 357 | 556 | 488 | 64 | 153 | 71 | 84 |

ND: Not determined

Nutrients of both these types proved to be beneficial for surfactant production. The range being most stimulating was 0.1 to 2.0% (wt/v). Nutrient broth increased the production of CMC quite effectively.

EXAMPLE 6

The initial pH of the broth before inoculation with culture SFC was adjusted respectively to 4.8, 5.4, 5.8, 6.3, 6.6, 8 and 9. This culture synthesizes two surfactants which can be identified by dilution to their specific CMC values. The broth medium used contained mineral salts and an optimum level of ammonium nitrate.

| pH | Biomass g/l | Surfactant Concentration × $CMC_1$ | × $CMC_2$ |
|---|---|---|---|
| 4.8 | 2.78 | 18,900 | 4,760 |
| 5.4 | 2.49 | 37,000 | 6,700 |
| 5.8 | 2.45 | 9,090 | 3,800 |
| 6.3 | 1.45 | 75 | 37 |
| 6.6 | .177 | 6.8 | 5.0 |
| 7.0 | ND | 270 | ND |
| 8.0 | ND | 243 | ND |
| 9.0 | ND | 243 | ND |

ND: Not determined

The optimal pH range appears to be between 4.8 and 5.8 but cannot be restricted within these levels. Maximum production occurred at pH 5.4.

EXAMPLE 7

Isonicotinic acid hydrazide (INH) (trade name: isoniazid) is used in treating tuberculosis, a disease caused by *Mycobacterium tuberculosis*. It specifically inhibits mycolic acid production. A test was set up in which INH was added to fermentation flasks at concentrations of 0, 0.1, 0.3, 0.5, 1.0, 3.0, and $5.0 \times 10^{-4}$ g/ml. A control series was run in which no INH was added. A third series was completed in which a 0.01% concentration of Tween 80 (a synthetic surfactant) was added to each vessel receiving INH. The results are summarized as follows:

| | Dilution Required to give 65 dynes/cm | |
|---|---|---|
| INH × $10^{-4}$ g/ml | Experimental | Experimental + .01% (w/v) Tween 80 |
| 0 | 5.06 | 9.49 |
| .1 | 3.3 | 17.08 |
| .3 | 2.0 | 11.39 |
| .5 | 1.5 | 9.49 |
| 1.0 | 2.0 | 7.59 |
| 3.0 | 1.5 | <1 |
| 5.0 | 1.0 | <1 |

0.01% Tween 80 requires a dilution of <1 to give 69 dynes/cm.

INH was shown to inhibit surfactant production at all levels tested. The first important discovery here is that a small amount of Tween 80, i.e. 0.01%, can double surfactant production by *Corynebacterium salvinicum*. Tween 80 (0.01%) not only reverses the effect of INH at concentrations up to $1 \times 10^{-4}$ g/ml, it also stimulates the synthesis of surfactant by the microbe at concentrations from 0.1 to $1.0 \times 10^{-4}$ g/ml. The improved synthesis of surfactant was as large as 3 times that of the control (no INH, no Tween 80). This observation is an important method of increasing the production of surfactant by cultures which produce mycolic acids, mycolic acid derivatives or related compounds.

EXAMPLE 8

The effect of the enzyme lysozyme on the growth and surfactant production by SFC was investigated. Lysozyme concentrations of 0.005% and 0.010% (w/v) were used, but the incubation was at 30° C. instead of 25°±2° C. The surfactant concentration with 0.010 (w/v) lysozyme (added to the flask) is about 1850×CMC compared to the 800×CMC obtained with the control sample. However, it was also shown that with SFC growing in the presence of 0.005% (w/v) lysozyme the surfactant concentration increases by a factor of more than 4 to a very high value of around 3,200×CMC. The concentration value obtained with 0.01% lysozyme in minimal medium without culture was less than 1×CMC. This value is an average of two separate but duplicate studies. The duration of growth in these studies was 3 days. The cell morphology changed quite dramatically with introduction of lysozyme. The cells rounded up and formed spheroplasts with both 0.005% and 0.01% lysozyme concentrations. However, the biomass values with 0.005% lysozyme were not much different from control, but with 0.01% lysozyme decreased by about 20%, indicating some lysis of cells. A batch fermentation of the surfactant hyperproducing SFC strain was carried out in a 14 liter New Brunswick fermentor. Again, 3% hexadecane was used as the carbon and energy source and fermentation was carried out at 30° C. An increase in surfactant concentration as well as increases in total biomass concentration and decreases in hydrocarbon concentrations and $O_2$ consumption were observed. Surfactant concentration peaked after about 43 hours of fermentation. The hexadecane concentration dropped rapidly after about 32 hours of fermentation. The highest biomass value reached was about 5.5 gm/l. A peak in surfactant concentration of about 1300×CMC was attained while the hydrocarbon concentration was reduced by about 73% during the course of the fermentation (about 70 hours). The doubling time of the microorganism was about 4 hours (specific growth rate $\mu = 0.17$ hrs.$^{-1}$).

EXAMPLE 9

The alkane oxidation inducer diethoxymethane (DEM) increases the production of surfactant by SFC. The concentration of surfactant produced was increased from 50×CMC to 65×CMC with the introduction of DEM. The concentration of DEM required for this ranges from 0.05 µg/ml to 5 µg/ml. However, the effect on cell morphology was quite pronounced. The cells tended to be even in size but in large aggregations. The total biomass increased by about 15% with the introduction of DEM.

EXAMPLE 10

Emulsification properties of lipid extract from *Corynebacterium salvinicum*, Strain SFC Emulsions were produced using the lipid extract emulsifier from SFC in combination with either an aliphatic hydrocarbon (n-hexadecane), an aromatic hydrocarbon (benzene) or wax. The emulsion drops were observed under the microscope. The emulsified hexadecane droplets ranged in size from about 1.5 µm to about 15 µm. The drops were found to be quite stable over several hours. Benzene is also easily emulsified into droplets. When viewed under the microscope, it was shown that the drops formed tend to aggregate into clumps. Such clumps have also been noted before with other aromatics such as p-xylene. It is believed that this aggregation makes aromatic hydrocarbon emulsions more stable. The wax emulsions show very unique features. The droplets are generally larger with bits of solidified wax inside them. This gives the appearance of multiple phase emulsions. The wax emulsions are quite stable for several hours.

When both aliphatic and aromatic emulsions were observed under the microscope using polarised light, presence of liquid crystalline regions in the emulsion drops were found. Symmetrical "illuminated" liquid crystalline regions of a hexadecane droplet were observed. The presence of these liquid crystalline regions in benzene droplets are easily shown. Wax droplets did not show these regions.

The presence of liquid crystalline regions signifies excess concentration of the emulsifying agent at the interface. It is correlated with increased stability of the emulsions.

The number of droplets with liquid crystalline regions was found to be slightly higher with the aromatic hydrocarbon than with the aliphatic (32% compared to 26% on averabe). It is believed that this is the first time that liquid crystalline regions in emulsion droplets have been prepared using microbial emulsifiers.

The presence of liquid crystalline regions was also noted when aliquots of hydrocarbon fermentation broth were observed microscopically under polarised light. Preparation can be made to show the "illuminated" crystalline regions in a fermentation broth of strain SFC grown on hexadecane for 3 days. The presence of cells inside the hydrocarbon phase are seen. The degree of crystallinity is proportional to the degree of "illumination" and regions of heavy crystallinity can be observed. It was observed that the liquid crystalline regions were more prevalent in the mid to late log phase broth than in the early log phase broth, suggesting the presence of excess emulsifier in the mid to late log phase. Dilution of the broth below the CMC value resulted in a marked reduction in the presence of liquid crystalline areas. This occurrence of liquid crystalline regions in fermentation broths has not been reported before.

A study of the effect of carbon chain length upon emulsification using the lipid extract from SFC revealed a curious picture. There is generally an increase in emulsification with chain length except for dips with $C_7$ and $C_{10}$, and emulsification levels off after $C_{14}$. These observations are quite different from the ones with the emulsifiers of other cultures and from those reported elsewhere. The results were obtained consistently and may reflect the chemical nature of the emulsifying agent(s) produced by SFC.

The PIT (Phase Inversion Temperature) value is a characteristic of a surfactant. An attempt was made to find the PIT value of the lipid extract from SFC. The inversion does not take place until a temperature of 100° C. Thus the lipid extract had a PIT value between 99°–100° C. This is a very high value, particularly for a biological emulsifier, and points to the usefulness of this emulsifier for formulating emulsions at high temperatures.

The importance of contact angles in studying surface phenomena is becoming increasingly evident. Thus the relation of contact angles to pathogenicity among microbes has been emphasized by previous work in the area. Contact angles also have relevance in hydrocarbon fermentations where they determine the ability of a microbe to utilize hydrocarbons as substrates for growth and maintenance. In this case, the role played by emulsifiers produced by the microbe is very significant. Contact angles were measured between the various phases involved in hydrocarbon fermentation involving *Corynebacterium salvinicum* Strain SFC as well as *Corynebacterium xerosis sp*. Contact angle for both cultures, lipid extract, etc. are shown in the example below. As can be seen, the contact angles involving the lipid extracts were very small or zero. Note also the reduction in contact angle between the cells and hexadecane when the lipid extract was dissolved in hexadecane. A smaller contact angle between the hydrocarbon containing the emulsifier and water would permit better emulsification. The comparisons with use of commercial emulsifiers show the potency of the biological emulsifiers. Using this method one can, perhaps, determine the potential capability of a microbe to grow on certain hydrophobic substrates, and also determine the influence of surfactants upon this capability and thus the relative ability of the microbial biosurfactant to wet biological surfaces.

| A. Contact angle measurements with/without lipid extract emulsifier from *Corynebacterium salvinicum* Strain SFC | | |
|---|---|---|
| | Surfaces | Contact Angle (°) |
| 1. | Cells – hexadecane | 23 |
| 2. | Cells – hexadecane + lipid extract | 0 |
| 3. | Cells – lipid extract | 0 |
| 4. | Glass – lipid extract | 1 |
| 5. | Glass – hexadecane | 30 |
| 6. | Cells – hexadecane + Tween 80 | 0 |
| 7. | Cells – supernatant | 2 |
| 8. | Glass – supernatant | 10 |

Index

The supernatant is the cell-free culture fluid from the fermentation broth of the microbe growing on 3% hexadecane for 3 days.

| B. Contact angle measurements with/without lipid extract emulsifier from *Corynebacterium xerosis* sp. | | |
|---|---|---|
| | Surfaces | Contact Angle (°) |
| 1. | Cells – hexadecane | 24 |
| 2. | Cells – hexadecane + lipid extract | 1 |
| 3. | Cells – lipid extract | 0 |
| 4. | Glass – lipid extract | 2 |
| 5. | Glass – hexadecane | 30 |
| 6. | Cells – hexadecane + Tween 80 | 0 |
| 7. | Cells – hexadecane + Span 20 | 1 |
| 8. | Cells – supernatant | 2 |
| 9. | Glass – supernatant | 9 |

Index

The supernatant is the cell-free culture fluid from the fermentation broth of the microbe growing on 3% hexadecane for 3 days.

A study was made to examine the surface active components of *Corynebacterium salvinicum*. The analysis was completed by making thin layer chromatographic analyses for various components. These were:

| | |
|---|---|
| Corynebacterium sp. SFC lipid extract | phosphatidylethanolamine, phosphatidyl serine, phosphatidyl glycerol, 1,2- and 1,3-diglycerides, triglyceride (high concentration), fatty acid/ester, a fluorescent component and two unknown components (digalactosyl diglyceride?). |

What we claim is:

1. A process for microbiological production of surfactant materials, which comprises cultivating by aerobic fermentation, in a growth promoting medium and under growth promoting conditions, and on a carbon-containing substrate, the microbial strain *Corynebacterium Salvinicum* strain SFC, said microbial strain being characterised by ability to metabolize the waxy protective coating of the plant cuticles of Salvinica water plant under normal growth conditions for the microbial strain, to produce a surfactant material of microbiological origin in said fermentation medium, and recovering the surfactant material so produced from said fermentation medium.

2. The process according to claim 1 wherein the fermentation broth includes a mixture of isonicotinic acid hydrazide and Tween 80, in effective amounts to increase the surfactant production.

3. The process according to claim 1 wherein the enzyme lysozyme is added to the cellular material produced during fermentation, to increase surfactant concentration.

4. The process according to claim 1 wherein the fermentation broth includes diethoxymethane.

5. The novel surfactant material of lipid-like structure possessing emulsification properties, resulting from the process of claim 1.

6. The process of claim 1 wherein the carbon-containing substrate is an aliphatic liquid hydrocarbon having from about 6 to about 18 carbon atoms per molecule.

* * * * *